(12) United States Patent
Friedlander et al.

(10) Patent No.: US 8,930,223 B2
(45) Date of Patent: Jan. 6, 2015

(54) PATIENT COHORT MATCHING

(75) Inventors: Robert R. Friedlander, Southbury, CT (US); Richard Hennessy, Austin, TX (US); James R. Kraemer, Santa Fe, NM (US)

(73) Assignee: International Business Machines Corporation, Armonk, NY (US)

( * ) Notice: Subject to any disclaimer, the term of this patent is extended or adjusted under 35 U.S.C. 154(b) by 212 days.

(21) Appl. No.: 13/436,239

(22) Filed: Mar. 30, 2012

(65) Prior Publication Data
US 2013/0262140 A1  Oct. 3, 2013

(51) Int. Cl.
*G06Q 50/00* (2012.01)
*G06Q 10/00* (2012.01)

(52) U.S. Cl.
USPC .................................................. 705/3; 705/2

(58) Field of Classification Search
USPC ...................................................... 705/2, 3, 4
See application file for complete search history.

(56) References Cited

U.S. PATENT DOCUMENTS

| | | | |
|---|---|---|---|
| 7,617,078 B2 * | 11/2009 | Rao et al. | 703/2 |
| 7,734,477 B2 | 6/2010 | Bellin et al. | |
| 7,761,440 B2 | 7/2010 | Chow et al. | |
| 7,792,776 B2 | 9/2010 | Friedlander et al. | |
| 7,792,783 B2 | 9/2010 | Friedlander et al. | |
| 7,809,660 B2 | 10/2010 | Friedlander et al. | |
| 7,917,478 B2 | 3/2011 | Friedlander et al. | |
| 8,121,858 B2 | 2/2012 | Friedlander et al. | |
| 2005/0043965 A1* | 2/2005 | Heller et al. | 705/2 |
| 2005/0060193 A1 | 3/2005 | Lancaster et al. | |
| 2005/0216312 A1* | 9/2005 | Bellin et al. | 705/3 |
| 2009/0043584 A1* | 2/2009 | Philips | 704/260 |
| 2009/0132460 A1 | 5/2009 | Alemi | |
| 2009/0265191 A1* | 10/2009 | Evanitsky | 705/4 |
| 2009/0292953 A1* | 11/2009 | Barghouthi et al. | 714/40 |
| 2009/0299766 A1 | 12/2009 | Friedlander et al. | |
| 2010/0217759 A1* | 8/2010 | Ma et al. | 707/719 |

(Continued)

FOREIGN PATENT DOCUMENTS

CN  102298662 A  12/2011
WO  WO 2006096603 A2 *  9/2006

OTHER PUBLICATIONS

Ross, Joseph S., "Statistical Models and Patient Predictors of Readmission for Heart Failure," Arch Intern Med, vol. 168, No. 13, Jul. 14, 2008.*
U.S. Appl. No. 13/275,483—Specification Filed Oct. 18, 2011.

(Continued)

*Primary Examiner* — Elaine Gort
*Assistant Examiner* — John Go
(74) *Attorney, Agent, or Firm* — John R. Pivnichny; Law Office of Jim Boice

(57) ABSTRACT

A computer hardware-implemented method, system, and/or computer program product matches a current patient to a specific patient readmission cohort. The specific patient readmission cohort, made up of patients having a shared attribute, has a historical likelihood of hospital readmission within a predefined post-discharge length of time for members of the specific patient readmission cohort. A database describing a current patient is selected, based on the cost and speed of accessing that database, as well as the probability that the database describes a similar attribute for the current patient as the shared attribute in the specific patient readmission cohort. If the current patient meets the requisite criteria for entry into the specific patient readmission cohort, then a recommendation designed to reduce a likelihood of hospital readmission of the current patient is generated.

13 Claims, 3 Drawing Sheets

(56) References Cited

U.S. PATENT DOCUMENTS

| | | |
|---|---|---|
| 2011/0106854 A1 | 5/2011 | Friedlander et al. |
| 2011/0295622 A1* | 12/2011 | Farooq et al. ............ 705/3 |
| 2011/0313788 A1 | 12/2011 | Amland et al. |
| 2012/0035954 A1 | 2/2012 | Yeskel |

OTHER PUBLICATIONS

U.S. Appl. No. 13/397,901—Specification Filed Feb. 16, 2012.
U.S. Appl. No. 12/907,346—Specification Filed Oct. 19, 2010.
J. Renton et al., "Factors Associated With Increased Risk of Readmission to Intensive Care in Australia," Springer, V. 37, N. 11, pp. 1800-1808, Published Online Aug. 16, 2011.
M. Hannah, "An Empirical Typology of Seriously Mentally Ill Patients Using Symptom and Social Functioning Factors," Dissertation, Dept. of Psychology, The University of Arizona, 1990, pp. 1-258.
PCT International Application No. PCT/IB2013/052145—International Search Report and Written Opinion Mailed Aug. 29, 2013.

* cited by examiner

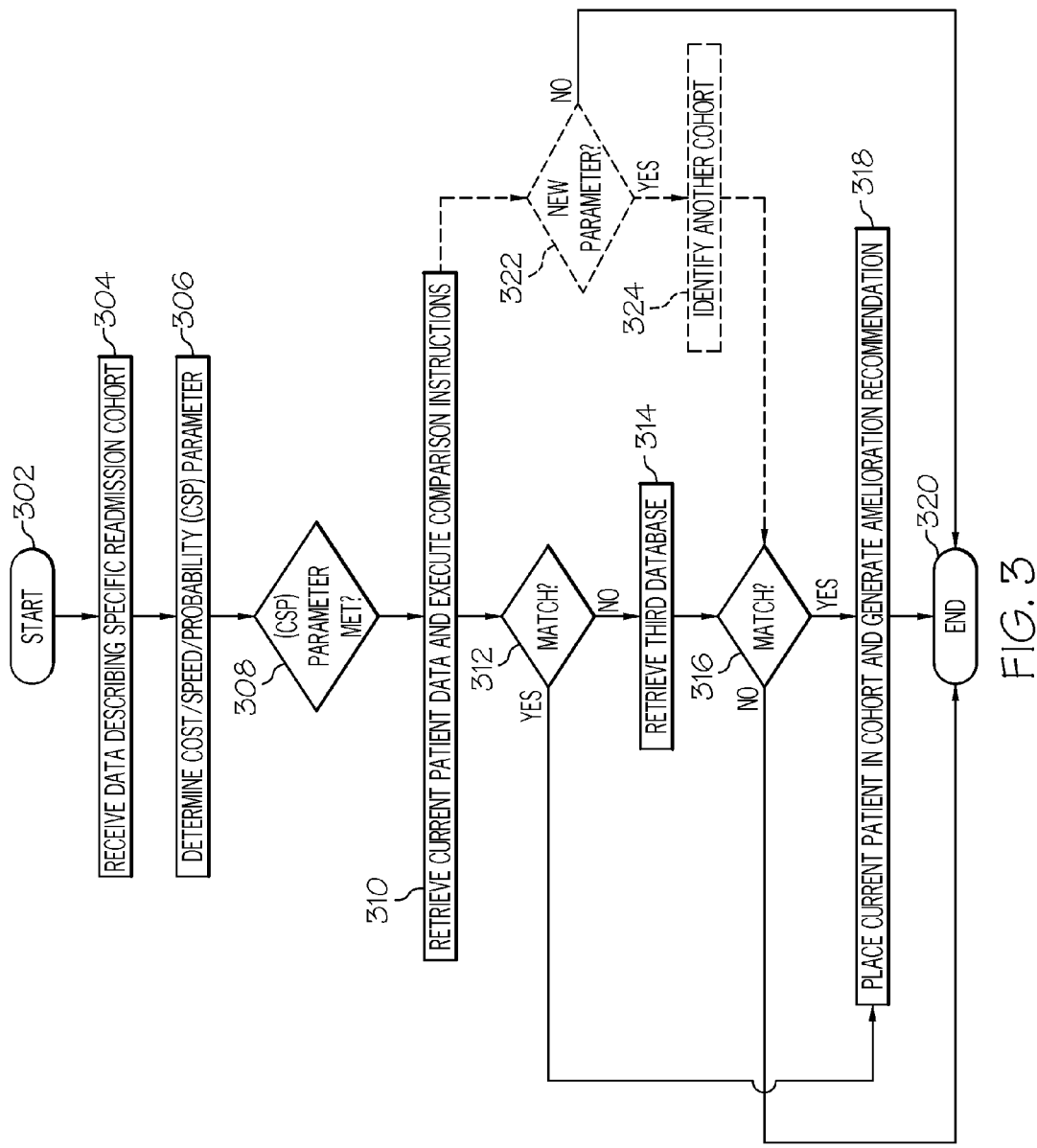

PATIENT COHORT MATCHING

BACKGROUND

The present disclosure relates to the field of computers, and specifically to the use of computers used in health care. Still more particularly, the present disclosure relates to the use of computers when determining a likelihood of a particular patient to be readmitted to a health care facility within a predefined period of time.

Electronic medical records (EMRs) are medical records describing medical patients and/or their medical treatment. Exemplary EMRs include hospital charts, health care providers' (doctors, nurses, therapists, etc.) notes, lab and x-ray reports, billing records, etc. These EMRs contain historical data, but have no inherent predictive properties.

SUMMARY

A computer hardware-implemented method, system, and/or computer program product matches a current patient to a specific patient readmission cohort. The specific patient readmission cohort, made up of patients having a shared attribute, has a historical likelihood of hospital readmission within a predefined post-discharge length of time for members of the specific patient readmission cohort. A database describing a current patient is selected, based on the cost and speed of accessing that database, as well as the probability that the database describes a similar attribute for the current patient as the shared attribute in the specific patient readmission cohort. If the current patient meets the requisite criteria for entry into the specific patient readmission cohort, then a recommendation designed to reduce a likelihood of hospital readmission of the current patient is generated.

BRIEF DESCRIPTION OF THE SEVERAL VIEWS OF THE DRAWINGS

FIG. 3 is a high level flow chart of one or more processes, executed by a computer system, to match a current patient to a specific patient readmission cohort.

DETAILED DESCRIPTION

Figure 1:
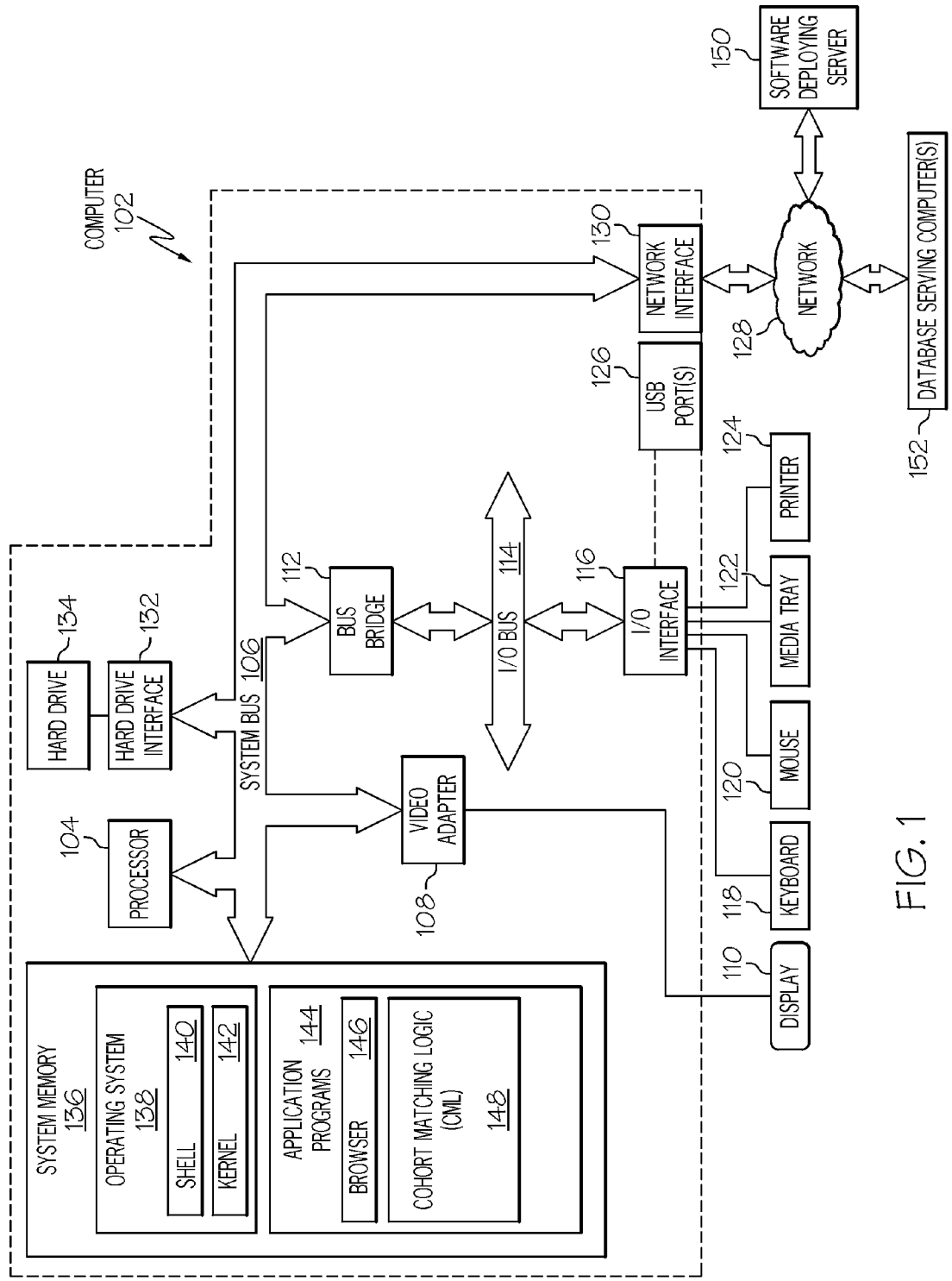
FIG. 1 depicts an exemplary system and network which may be used to implement the present invention.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including, but not limited to, wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

With reference now to the figures, and in particular to FIG. 1, there is depicted a block diagram of an exemplary system and network that may be utilized by and/or in the implementation of the present invention. Note that some or all of the exemplary architecture, including both depicted hardware and software, shown for and within computer 102 may be utilized by software deploying server 150 and/or database serving computer(s) 152.

Exemplary computer 102 includes a processor 104 that is coupled to a system bus 106. Processor 104 may utilize one or more processors, each of which has one or more processor cores. A video adapter 108, which drives/supports a display 110, is also coupled to system bus 106. System bus 106 is coupled via a bus bridge 112 to an input/output (I/O) bus 114. An I/O interface 116 is coupled to I/O bus 114. I/O interface 116 affords communication with various I/O devices, including a keyboard 118, a mouse 120, a media tray 122 (which may include storage devices such as CD-ROM drives, multimedia interfaces, etc.), a printer 124, and external USB port(s) 126. While the format of the ports connected to I/O interface 116 may be any known to those skilled in the art of computer architecture, in one embodiment some or all of these ports are universal serial bus (USB) ports.

As depicted, computer 102 is able to communicate with a software deploying server 150, as well as database serving computer(s) 152, using a network interface 130. Network interface 130 is a hardware network interface, such as a network interface card (NIC), etc. Network 128 may be an external network such as the Internet, or an internal network such as an Ethernet or a virtual private network (VPN).

A hard drive interface 132 is also coupled to system bus 106. Hard drive interface 132 interfaces with a hard drive 134. In one embodiment, hard drive 134 populates a system memory 136, which is also coupled to system bus 106. System memory is defined as a lowest level of volatile memory in computer 102. This volatile memory includes additional higher levels of volatile memory (not shown), including, but not limited to, cache memory, registers and buffers. Data that populates system memory 136 includes computer 102's operating system (OS) 138 and application programs 144.

OS 138 includes a shell 140, for providing transparent user access to resources such as application programs 144. Generally, shell 140 is a program that provides an interpreter and an interface between the user and the operating system. More specifically, shell 140 executes commands that are entered into a command line user interface or from a file. Thus, shell 140, also called a command processor, is generally the highest level of the operating system software hierarchy and serves as a command interpreter. The shell provides a system prompt, interprets commands entered by keyboard, mouse, or other user input media, and sends the interpreted command(s) to the appropriate lower levels of the operating system (e.g., a kernel 142) for processing. Note that while shell 140 is a text-based, line-oriented user interface, the present invention will equally well support other user interface modes, such as graphical, voice, gestural, etc.

As depicted, OS 138 also includes kernel 142, which includes lower levels of functionality for OS 138, including providing essential services required by other parts of OS 138 and application programs 144, including memory management, process and task management, disk management, and mouse and keyboard management.

Application programs 144 include a renderer, shown in exemplary manner as a browser 146. Browser 146 includes program modules and instructions enabling a world wide web (WWW) client (i.e., computer 102) to send and receive network messages to the Internet using hypertext transfer protocol (HTTP) messaging, thus enabling communication with software deploying server 150 and other computer systems.

Application programs 144 in computer 102's system memory (as well as software deploying server 150's system memory) also include a cohort matching logic (CML) 148. CML 148 includes code for implementing the processes described below, including those described in FIGS. 2-3. In one embodiment, computer 102 is able to download CML 148 from software deploying server 150, including in an on-demand basis, wherein the code in CML 148 is not downloaded until needed for execution. Note further that, in one embodiment of the present invention, software deploying server 150 performs all of the functions associated with the present invention (including execution of CML 148), thus freeing computer 102 from having to use its own internal computing resources to execute CML 148.

Note that the hardware elements depicted in computer 102 are not intended to be exhaustive, but rather are representative to highlight essential components required by the present invention. For instance, computer 102 may include alternate memory storage devices such as magnetic cassettes, digital versatile disks (DVDs), Bernoulli cartridges, and the like. These and other variations are intended to be within the spirit and scope of the present invention.

Figure 2:
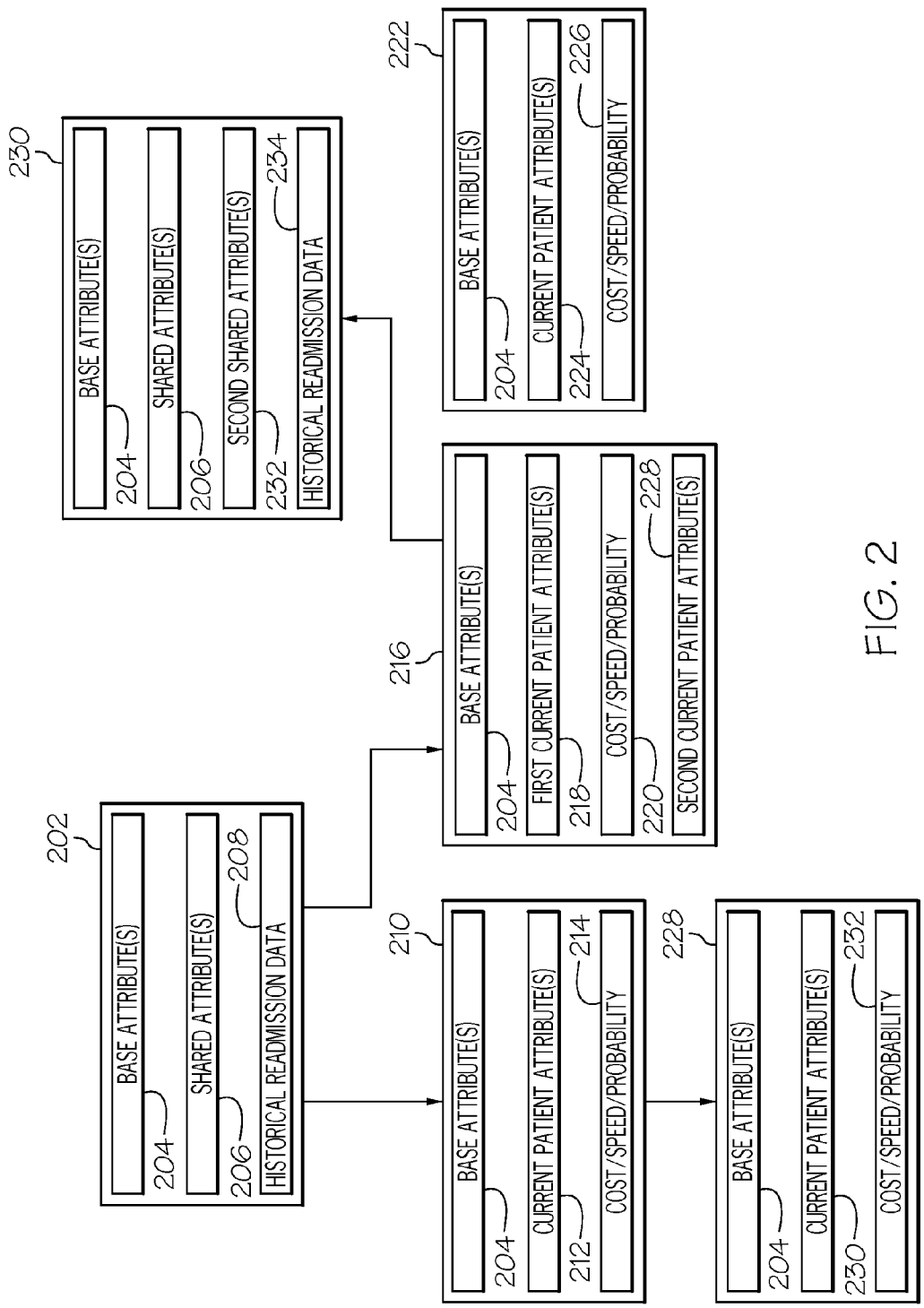
FIG. 2 illustrates relationships among databases that describe patient readmission cohorts and other patient databases.

With reference now to FIG. 2, relationships among databases that describe patient readmission cohorts and other patient databases are presented. Note that all databases depicted in FIG. 2 may be accessed by the database serving computers 152 depicted in FIG. 1. For example, consider first database 202, which contains a first set of binary data that describes a set of patients. Together, these patients make up a patient readmission cohort. The first database includes base attribute(s) 204, which is discussed below. The first database also includes shared attribute(s) 206, which are one or more medical attributes that are shared by all members of the specific patient readmission cohort that is described in first database. Also part of the first database 202 is an historical readmission data 208 that describes a history of hospital re-admittance (to the same or another hospital), or a history of other post-discharge and unexpected medical care, for members of the patient readmission cohort. For example, assume for exemplary purposes that the base attribute(s) 204 is that all members of this cohort have been discharged from a particular surgical ward in a particular hospital. The shared attribute(s) 206 may be that all members of this cohort had coronary artery bypass surgery, and they all have a genetic defect at a particular gene in their human genomes. Within these parameters, historical data found in historical readmission data 208 shows that 80% of all members of the patient readmission cohort described in the first database 202 were readmitted to the hospital within 30 days.

In the example just presented, determining whether or not a current patient had coronary artery bypass surgery is probably simple to glean from electronic medical records (EMRs). However, determining whether that current patient has the genetic defect at the particular gene is likely to be more difficult to derive from EMRs or other databases, unless the other database contains results of gene sequencing for that current patient. Such tests, and their resulting databases, may be too expensive to access. Therefore, a decision is made to search for a database that is fast to access, is cheap to access, and has a predetermined probability of containing information needed to describe the genetic defect that afflicts members of the patient readmission cohort described in first database 202. This predetermined probability is less than 100% (as it would be if the data was from a genome study), but is still deemed to provide sufficient evidence (beyond some predetermined level of confidence) to demonstrate the existence of the genetic defect. For example, information that indicates the presence of this defective gene in the current patient may be derived from secondary tests, such as lab tests that indicate the presence of enzymes produced by the defective gene, at some predetermined probability of accurately describing the defective gene (e.g., 90%). Note that the combination cost/speed/probability parameter is thus a matrix of cost, speed and probability, where each parameter (cost/speed/probability) may be independently weighted.

Assume now that a determination has been made that second database 210, which holds data describing the same base attribute(s) 204 found in the first database 202, and has its own speed/cost/probability parameter 220, contains data that is within a predefined probability of accuracy for defining current patient attribute(s) 212 that substantively match the shared attribute(s) 206 for the patient readmission cohort. As noted above, this probability of accuracy is part of the cost/speed/probability parameter discussed above. Assume also that first database 202 meets the speed and cost parameters set by the cost/speed/probability parameter discussed above. As depicted in FIG. 2, database 216 and database 222 also contain the base attribute(s) 204 found in the first database 202, as well as other patient attributes (e.g., elements 218, 228, and/or 224) for the current patient. However, database 216 and/or database 222 do not match the cost/speed/probability parameter as well as database 210 (i.e., they are more expensive, slower, and/or less likely to have data that describes the shared attribute(s) 206 than database 210). As such, database 210 is selected as the best candidate for determining whether the current patient has the same attribute(s) as the shared attribute(s) 206 of the patient readmission cohort described in database 202.

Current patient attribute(s) 212 is then compared to shared attribute(s) 206, using a matching algorithm that determines whether the information in current patient attribute(s) 212 adequately describes the same attribute found in shared attribute(s) 206. If it does, then the current patient is placed into the patient readmission cohort. If it does not, then the process either ends, or else another database 228, which has other current patient attribute(s) 230 (e.g., the current patient having a family history of the defective gene) is also accessed (while information gleaned from database 210 is still retained). Note that this third database 228 may have a cost/speed/probability parameter 232 that is the same as, or is different from, the cost/speed/probability parameter 214 for the second database 210. If examining/evaluating both the current patient attribute(s) 212 and current patient attribute(s) 230 in comparison to the shared attribute(s) 206 still does not resolve whether or not the current patient has the same attribute(s) as the shared attribute(s) 206, then another database can be accessed, or else the search for other databases ends, and an alert is sent out that the patient cannot be placed within the specific patient readmission cohort described by the first database 202. However, if examining/evaluating both the current patient attribute(s) 212 and current patient attribute(s) 230 in comparison to the shared attribute(s) 206 establishes that the current patient belongs to the specific patient readmission cohort described by the first database 202, then the current patient is placed in that cohort.

In one embodiment, the third database 228 is derived from the second database 210. For example, assume that a second set of binary data (i.e., the data from database 210) is retrieved from an electronic medical records database. In this example, the third set of binary data (found in database 228), which describes the first current patient attribute for the current patient, is created by data mining text in the second set of binary data. For example, a phrase such as "family history" may be searched for within the database 210. If the current patient attribute(s) 212 described in one embodiment herein only dealt with laboratory results showing serological markers for a defective gene, there may have been no prior search for data related to a family history of this genetic defect. However, a text search/data mining of database 210 may indicate that a significant (i.e., more than a predetermined percentage) number of the members of the patient readmission cohort described by database 202 have a family history of this genetic defect. This text search/data mining thus leads to the creation of the third database 228.

Note again that database 222, which has its own set of current patient attribute(s) 224 (which may be the same or different attributes as current patient attribute(s) 212 found in database 210), and its own cost/speed/probability parameters 226 (which are unique as compared to the cost/speed/probability parameters found in the other secondary databases 210, 216, and 228) was not selected, since its cost/speed/probability parameters 226 did not optimally meet the predefined parameter values (i.e., the minimum speed, maximum cost, and maximum probability of success that has been predetermined to be acceptable).

Assume now that rather than selecting database 210, database 216 was selected for examination. Assume also that while mining/scrutinizing the first current patient attribute(s) 218 in database 216, a second current patient attribute(s) 228 was discovered. This second current patient attribute(s) 228 describes an attribute that either provides addition details about the first current patient attribute(s) 218 (e.g., evidence of ribonucleic acid (RNA) that is typically associated with the defective gene associated with the first current patient attribute(s) 218), or else second current patient attribute(s) 228 describes an unrelated attribute (e.g., elevated blood sugar, if not actual diabetes) of the current patient. Using this new information described by the second current patient attribute(s) 228, another patient readmission cohort may be identified, such as that described in database 230. If a determination is then made that it would be faster and/or cheaper and/or have a higher likelihood of assigning the current patient to this other patient readmission cohort, then the first current patient attribute(s) 218 and second current patient attribute(s) 228 are compared to respective shared attribute(s) 206 and second shared attribute(s) 232 found in database 230. In one embodiment, the historical readmission data 208 and the historical readmission data 234 are also compared to one another, such that whichever patient readmission cohort had a higher incidence of readmission (e.g., 90% readmission rates within 30 days of discharge) is selected over another patient readmission cohort with a lower incidence of readmission (e.g., 75% readmission rates within 30 days of discharge). By selecting the higher-readmission patient cohort, additional confidence is created that readmission incidents can be reduced (due to recommended amelioration).

Note that in one embodiment described herein, the specific patient readmission cohort is selected from a plurality of patient readmission cohorts. For example, assume that there are three patient readmission cohorts, each of which has data describing two patient attributes. A first patient readmission cohort may include data describing patients that were admitted to "Hospital A" and had coronary artery bypass surgery. A second patient readmission cohort may include data describing patients that were admitted to "Hospital A" and had a broken bone reset. A third patient readmission cohort may include data describing patients that were admitted to "Hospital A" and had liposuction. If the current patient was admitted to "Hospital A" and had coronary artery bypass surgery, then the current patient will be compared to the first patient readmission cohort, using another attribute (e.g., a defective gene) found in parameters of the first patient readmission cohort. In one embodiment, the patient readmission cohort is also selected according to which patient readmission cohort has the highest readmission incidence rate, as discussed above.

With reference now to FIG. 3, a high level flow chart of one or more processes, executed by a computer system, to match a current patient to a specific patient readmission cohort is presented. After initiator block 302, a first set of binary data that describes a specific patient readmission cohort is received (block 304). As described herein, the first set of binary data, which is from a first database (e.g., database 202 depicted in FIG. 2) describes a shared attribute of patients in the specific patient readmission cohort. These shared attributes may be a common diagnosis of a disease or physical injury; a common surgical procedure, medication, therapy, and/or other medical treatment; a common location of treatment (e.g., the cohort members were all treated at a same hospital, a same ward, and/or a same department, etc.); a common health care provider of treatment (e.g., the cohort members were treated by a same physician, nurse, therapist, pharmacist, etc.); a common family history (e.g., all cohort members have parents who have a particular gene defect); etc. The first set of binary data also includes/describes an historical likelihood of hospital readmission within a predefined post-discharge length of time for members of the specific patient readmission cohort, as found in the historical readmission data 208 shown in FIG. 2.

As depicted in block 306, a cost/speed/probability parameter for a second database that contains a second set of binary data is determined. This cost/speed/probability parameter (such as cost/speed/probability parameter 214 found in the second database 210 in FIG. 2) defines 1) a minimum probability that the second database contains data that describes a first current patient attribute for a current patient; 2) a first maximum cost to access the second database; and 3) a first minimum speed to access the second database. That is, the cost parameter portion of the cost/speed/probability parameter describes how expensive it will be in monetary cost, computer type, network time, etc. to access this particular database. The speed parameter portion of the cost/speed/probability parameter describes how much time it will take (e.g., a few milliseconds or several minutes) to access this particular database. The probability parameter portion of the cost/speed/probability parameter describes what the probability/likelihood (e.g. 95%) that this particular database will contain data about the current patient (i.e., the first current patient attribute—e.g., current patient attribute(s) 212 shown in FIG. 2) that matches the shared attribute (e.g., shared attribute(s) 206 of the patient readmission cohort depicted/ described by database 202 in FIG. 2) within a predefined level of certainty. This "predefined level of certainty" describes how closely and/or to what level of certainty the current patient attribute(s) matches the shared attribute(s) of the cohort. For example, assume that the data about the current patient is related to serological markers for a genetic defect. Assume further that these markers are 70% accurate in demonstrating the presence of the genetic defect. If the predefined level of certainty is "anything over 60%", then the process will accept these serological markers for the current patient as sufficient evidence that the current patient has the same genetic defect (shared attribute) as patients in the patient readmission cohort.

In one embodiment, the "predefined level of certainty" is derived from a point system. That is, a separate point value is assigned for each entry in the second set of binary data and the third set of binary data. These point values describe an amount of information about the first current patient attribute. For example, assume that a first set of binary data contains the results of a full genome examination for the current patient, thus providing conclusive evidence of a genetic defect in this current patient. This first set of binary data would be assigned a high point value (e.g., 1000). A second set of binary data may contain lab results, which indicates serological markers indicative of the genetic defect in the current patient. This second set of binary data would be assigned a lower point value (e.g., 50), since the serological markers are not conclusive. A third set of binary data may only contain chart notes (e.g., from a gross physical examination) that merely suggest that the current patient has the genetic defect. This third set of binary data would therefore be assigned an even lower point value (e.g., 25). Assume now that only if a total point count (e.g., 75) is reached will there be the level of certainty that the patient actually has the genetic defect. While the first set of binary data (having a point value of 1000) would clearly exceed the minimum required point count of 75, it is likely "overkill", since such data is very expensive to generate. However, the combination of points (25 and 50) from the respective second and third sets of binary data meet the 75 point minimum, thus indicating that these two sets of binary data (together) meet the minimum predefined level of certainty.

With reference now to query block 308 in FIG. 3, a query is made to determine whether the cost/speed/probability parameter for a candidate second database (that may contain information about the current patient) is met. If so, then data about the current patient is retrieved from that second database for comparison with the shared attribute(s) of the patient readmission cohort (block 310). This comparison is performed by using a first set of binary data (that describes the patient readmission cohort) and a second set of binary data (that describes the current patient) as inputs to comparison computer instructions that determine whether the second database contains data for the current patient that matches the shared attribute of patients in the specific patient readmission cohort within the predefined level of certainty. If there is a match within this predefined level of certainty (query block 312), then the current patient is placed within that specific patient readmission cohort, and a recommendation for amelioration (i.e., taking steps to reduce the likelihood of the current patient being readmitted with a predefined period of time) is made (block 318). In this embodiment, the process ends at terminator block 320.

Examples of the amelioration that is recommended include, but are not limited to, the following embodiments. In one embodiment, rather than discharge the patient on the scheduled discharge date, the patient stays in the hospital for the extended length of treatment. In another embodiment, the amelioration is an extended length of treatment by a non-hospital health care facility beyond a discharge date for the current patient. In another embodiment, the amelioration is an extended length of treatment by a non-hospital health care provider beyond a discharge date for the current patient. That is, follow-up care may be provided by the discharging hospital, and/or follow-up care may be provided outside of the hospital, by a home health care provider, a rehabilitation center, etc. In another embodiment, the amelioration is additional medical testing before discharging the current patient from a hospital. That is, before discharging the patient from the hospital, additional lab/x-ray/examination tests are run on the patient, in order to determine whether there are any conditions that have been overlooked while admitted to the hospital.

Returning to query block 312, if there is not a match, within the predefined level of certainty, between the current patient attribute(s) and the shared attribute(s) of members of the patient readmission cohort, then a third database is retrieved (block 314). That is, in response to the execution of comparison computer instructions failing to place the current patient into the specific patient readmission cohort within the predefined level of certainty, a third set of binary data (e.g., current patient attribute(s) 230 from the third database 228 shown in FIG. 2) that further describes the first current patient attribute for the current patient is retrieved. Note that the third set of binary data meets a second cost/speed/probability parameter, which may be different from the first cost/speed/probability parameter of the second database (i.e., the first current patient database that was previously accessed). As with the first cost/speed/probability parameter, the second cost/speed/probability parameter defines a second minimum probability that the third database contains data that describes the first current patient attribute for the current patient. Similarly, the second cost/speed/probability parameter defines a second maximum cost and a second minimum speed to access the third database.

As shown in query block 316, comparison computer instructions are executed to compare the first set of binary data with the second set of binary data and the third set of binary data, by using the first, second and third sets of binary data as inputs to the comparison computer instructions. That is, a combination of the information found in the second and third sets of binary data (both related to the current patient) is compared to the information for members of the patient readmission cohort (found in the first database). In response to there being a match within the predefined level of certainty, the current patient is placed into the specific patient readmission cohort, and a recommendation for ameliorating (reducing) a likelihood of hospital readmission of the current patient within a predefined post-discharge length of time is generated (block 318). In one embodiment, the process thus ends at terminator block 320.

Returning to query block 316, if there still is no match, then the process will end at terminator block 320, assuming that no further searches for current patient databases are warranted. However, before giving up, a search may be made for another database that was not previously considered. That is, assume that all databases previously considered were from electronic medical records databases (i.e., computer records of hospital charts, lab results, etc.) There may nonetheless be other databases, such as work history databases, travel history databases, etc. that may be useful in determining if the current patient belongs in a specific patient readmission cohort. Thus, in response to executing said comparison computer instructions, with the first, second, and third sets of binary data as inputs, failing to place the current patient into the specific patient readmission cohort within the predefined level of certainty, a fourth set of binary data is retrieved. This fourth set of binary data further describes the first current patient attribute for the current patient, and is retrieved from a fourth database that is not part of the electronic medical records database.

Note further that if there is no match in query block 316, in one embodiment an alert is generated indicating that the current patient has not been placed into any patient readmission cohort (or at least the specific patient readmission cohort such as that described in database 202).

Returning to block 310, assume that the search of the second database (containing information about the current patient) reveals a new parameter (query block 322). This new parameter (e.g., the second current patient attribute(s) 228 in FIG. 2) was not found in the patient readmission cohort that has been used before (e.g., the patient readmission cohort described in the first database 202 in FIG. 2), but is found in another cohort (e.g., the second patient readmission cohort described in database 230 in FIG. 2). As such, this second patient readmission cohort may turn out to be better than the first patient readmission cohort. That is, the second patient readmission cohort 1) may have a higher accuracy of predicting readmissions (e.g., the likelihood of readmission based on the historical readmission data 234 is greater than the likelihood based on the historical readmission data 208 shown in FIG. 2); 2) be a better patient readmission cohort since accessing database 216 is cheaper/faster/more reliable (according to is cost/speed/probability parameter 220 shown in FIG. 2) than other current patient databases; 3) may have a higher readmission rate (and thus is more critical); etc. If so, then the other patient readmission cohort is identified (block 324), and a determination is made as to whether the new current patient data matches up with this other patient readmission cohort (query block 316). Thus, in this embodiment, in response to said retrieving the second set of binary data identifying a second current patient attribute for the current patient, another patient readmission cohort is identified. The second current patient attribute is depicted by a fourth set of binary data, and another patient readmission cohort is depicted by a fifth set of binary data that describes the first and second current patient attributes for the current patient. In response to executing comparison computer instructions, with the second, fourth, and fifth sets of binary data as inputs, placing the current patient into the other patient readmission cohort within another predefined level of certainty, a recommendation for another amelioration to reduce the likelihood of hospital readmission of the current patient within the predefined post-discharge length of time is generated.

As described herein, the present invention optimizes, according to cost, time (speed), and trust (reliability), a determination as to whether a particular patient is a member of a particular patient readmission cohort. This optimization is achieved by selecting a client parameter database, which best meets predetermined cost/speed/probability parameters, from multiple client parameter databases. Note further that the multiple client parameter databases (and the data that populates them) may be homogenous (i.e., from similar sources such as EMRs), or they may be heterogeneous (i.e., from different types of sources, such as written text entries in a hospital chart, from lab test results, from family history records, from travel records (e.g., visa/passport records), from work histories (e.g., from payroll records), etc. That is, in one embodiment the data used to populate the current patient's parameter database may come from both medical as well as non-medical database sources, which may be in the same or different formats.

The flowchart and block diagrams in the figures illustrate the architecture, functionality, and operation of possible implementations of systems, methods and computer program products according to various embodiments of the present disclosure. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of various embodiments of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

Note further that any methods described in the present disclosure may be implemented through the use of a VHDL (VHSIC Hardware Description Language) program and a VHDL chip. VHDL is an exemplary design-entry language for Field Programmable Gate Arrays (FPGAs), Application Specific Integrated Circuits (ASICs), and other similar electronic devices. Thus, any software-implemented method described herein may be emulated by a hardware-based VHDL program, which is then applied to a VHDL chip, such as a FPGA.

Having thus described embodiments of the invention of the present application in detail and by reference to illustrative embodiments thereof, it will be apparent that modifications and variations are possible without departing from the scope of the invention defined in the appended claims.

What is claimed is:

1. A computer hardware-implemented method of matching a current patient to a specific patient readmission cohort, the computer hardware-implemented method comprising:

receiving, by one or more computer processors, from a first database, a first set of binary data that describes a shared attribute of patients of a specific patient readmission cohort and a historical likelihood of hospital readmission within a predefined post-discharge length of time;

determining, by one or more computer processors, a first cost/speed/probability parameter for a second database, wherein the first cost/speed/probability parameter comprises a first minimum probability that the second database contains a second set of binary data that describes a current patient attribute for a current patient, wherein the first minimum probability is less than 100% but greater than 50%, and wherein the first cost/speed/probability parameter further comprises a first maximum cost and a first minimum speed to access the second database;

assigning, by one or more computer processors, a first point value to the first cost/speed/probability parameter;

determining, by one or more computer processors, that the first cost/speed/probability parameter meets or exceeds a first threshold for the first point value;

in response to the first cost/speed/probability parameter meeting or exceeding the first threshold for the first point value, retrieving, by one or more computer processors, the second set of binary data from the second database;

assigning, by one or more computer processors, a second point value to the second binary data based on the amount of information contained in the second binary data;

determining, by one or more computer processors, that the second binary data does not meet or exceed a second threshold for the second point value;

in response to the second binary data failing to meet or exceed the second threshold for the second point value:

determining, by one or more computer processors, a second cost/speed/probability parameter for a third database, wherein the second cost/speed/probability parameter comprises a second minimum probability that the third database contains a third set of binary data that describes the current patient attribute for the current patient, wherein the second minimum probability is less than 100% but greater than 50%, and wherein the second cost/speed/probability parameter further comprises a second maximum cost and a second minimum speed to access the third database;

assigning, by one or more computer processors, a third point value to the second cost/speed/probability parameter;

determining, by one or more computer processors, that the second cost/speed/probability parameter meets or exceeds a third threshold for the third point value;

in response to the second cost/speed/probability parameter meeting or exceeding the third threshold for the third point value, retrieving, by one or more computer processors, the third set of binary data from the third database;

assigning, by one or more computer processors, a fourth point value to the third binary data based on the amount of information contained in the third binary data;

summing, by one or more computer processors, the second and fourth point values;

determining, by one or more computer processors, that the summation of the second and fourth point values exceeds a fourth threshold;

in response to determining that the summation of the second and fourth point values exceeds the fourth threshold, placing, by one or more computer processors, the current patient into the specific patient readmission cohort; and recommending, by one or more computer processors, an amelioration based on the specific patient readmission cohort to reduce a likelihood of hospital readmission of the current patient within the predefined post-discharge length of time.

2. The computer hardware-implemented method of claim 1, wherein the amelioration is treatment by a non-hospital health care facility beyond a discharge date for the current patient.

3. The computer hardware-implemented method of claim 1, wherein the amelioration is treatment by a non-hospital health care provider beyond a discharge date for the current patient.

4. The computer hardware-implemented method of claim 1, wherein the amelioration is additional medical testing before discharging the current patient from a hospital.

5. The computer hardware-implemented method of claim 1, wherein the second set of binary data is retrieved from an electronic medical records database, and wherein the computer hardware-implemented method further comprises:

creating, by one or more computer processors, the third set of binary data that describes the first current patient attribute for the current patient by data mining text in the second set of binary data.

6. The computer hardware-implemented method of claim 1, further comprising:

determining that the second cost/speed/probability parameter fails to meet or exceed the third threshold for the third point value;

in response to determining that the second cost/speed/probability parameter fails to meet or exceed the third threshold for the third point value, transmitting, by one or more computer processors, an alert that the current patient has not been placed into the specific patient readmission cohort.

7. The computer hardware-implemented method of claim 1, wherein the specific patient readmission cohort is selected from a plurality of patient readmission cohorts, wherein each of the plurality of patient readmission cohorts is defined as having multiple patient attributes, and wherein the computer hardware-implemented method further comprises:

identifying, by one or more computer processors, at least one known attribute about the current patient; and selecting, by one or more computer processors, the specific patient readmission cohort from a plurality of patient readmission cohorts by matching said at least one known attribute about the current patient to at least one of the multiple patient attributes in the patient readmission cohort.

8. A computer program product matching a current patient to a specific patient readmission cohort, the computer program product comprising:

a non-transitory computer readable storage media;

first program instructions to receive, from a first database, a first set of binary data that describes a shared attribute of patients of a specific patient readmission cohort and a historical likelihood of hospital readmission within a predefined post-discharge length of time;

second program instructions to determine a first cost/speed/probability parameter for a second database, wherein the first cost/speed/probability parameter comprises a first minimum probability that the second database contains a second set of binary data that describes a current patient attribute for a current patient, wherein the first minimum probability is less than 100% but greater than 50%, and wherein the first cost/speed/probability parameter further comprises a first maximum cost and a first minimum speed to access the second database;

third program instructions to assign a first point value to the first cost/speed/probability parameter;

fourth program instructions to determine that the first cost/speed/probability parameter meets or exceeds a first threshold for the first point value;

fifth program instructions to, in response to the first cost/speed/probability parameter meeting or exceeding the first threshold for the first point value, retrieve the second set of binary data from the second database;

sixth program instructions to assign a second point value to the second binary data based on the amount of information contained in the second binary data;

seventh program instructions to determine that the second binary data does not meet or exceed a second threshold for the second point value;

eighth program instructions to, in response to the second binary data failing to meet or exceed the second threshold for the second point value:

determine a second cost/speed/probability parameter for a third database, wherein the second cost/speed/probability parameter comprises a second minimum probability that the third database contains a third set of binary data that describes the current patient attribute for the current patient, wherein the second minimum probability is less than 100% but greater than 50%, and wherein the second cost/speed/probability parameter-further comprises a second maximum cost and a second minimum speed to access the third database;

ninth program instructions to assign a third point value to the second cost/speed/probability parameter;

tenth program instructions to determine that the second cost/speed/probability parameter meets or exceeds a third threshold for the third point value;

eleventh program instructions to, in response to the second cost/speed/probability parameter meeting or exceeding the third threshold for the third point value, retrieve the third set of binary data from the third database;

twelfth program instructions to assign a fourth point value to the third binary data based on the amount of information contained in the third binary data;

thirteenth program instructions to sum the second and fourth point values;

fourteenth program instructions to determine that the summation of the second and fourth point values exceeds a fourth threshold;

fifteenth program instructions to, in response to determining that the summation of the second and fourth point values exceeds the fourth threshold, place the current patient into the specific patient readmission cohort; and sixteenth program instructions to generate a recommendation for an amelioration based on the specific patient readmission cohort to reduce a likelihood of hospital readmission of the current patient within the predefined post-discharge length of time;

and wherein the first, second, third, fourth, fifth, sixth, seventh, eighth, ninth, tenth, eleventh, twelfth, thirteenth, fourteenth, fifteenth, and sixteenth program instructions are stored on the non-transitory computer readable storage media.

9. The computer program product of claim 8, further comprising:
seventeenth program instructions to, in response to determining that the second cost/speed/probability parameter fails to meet or exceed the third threshold for the third point value, transmit an alert that the current patient has not been placed into the specific patient readmission cohort;
and wherein the seventeenth program instructions are stored on the non-transitory computer readable storage media.

10. The computer program product of claim 8, wherein the specific patient readmission cohort is selected from a plurality of patient readmission cohorts, wherein each of the plurality of patient readmission cohorts is defined as having multiple patient attributes, and wherein the computer program product further comprises:
seventeenth program instructions to identify at least one known attribute about the current patient; and
eighteenth program instructions to select the specific patient readmission cohort from a plurality of patient readmission cohorts by matching said at least one known attribute about the current patient to at least one of the multiple patient attributes in the patient readmission cohort;
and wherein the seventeenth and eighteenth program instructions are stored on the non-transitory computer readable storage media.

11. A system comprising:
a computer processor, a computer readable memory, and a computer readable storage media;
first program instructions to receive, from a first database, a first set of binary data that describes a shared attribute of patients of a specific patient readmission cohort and a historical likelihood of hospital readmission within a predefined post-discharge length of time;
second program instructions to determine a first cost/speed/probability parameter for a second database, wherein the first cost/speed/probability parameter comprises a first minimum probability that the second database contains a second set of binary data that describes a current patient attribute for a current patient, wherein the first minimum probability is less than 100% but greater than 50%, and wherein the first cost/speed/probability parameter further comprises a first maximum cost and a first minimum speed to access the second database;
third program instructions to assign a first point value to the first cost/speed/probability parameter;
fourth program instructions to determine that the first cost/speed/probability parameter meets or exceeds a first threshold for the first point value;
fifth program instructions to, in response to the first cost/speed/probability parameter meeting or exceeding the first threshold for the first point value, retrieve the second set of binary data from the second database;
sixth program instructions to assign a second point value to the second binary data based on the amount of information contained in the second binary data;
seventh program instructions to determine that the second binary data does not meet or exceed a second threshold for the second point value;
eighth program instructions to, in response to the second binary data failing to meet or exceed the second threshold for the second point value:
determine a second cost/speed/probability parameter for a third database, wherein the second cost/speed/probability parameter comprises a second minimum probability that the third database contains a third set of binary data that describes the current patient attribute for the current patient, wherein the second minimum probability is less than 100% but greater than 50%, and wherein the second cost/speed/probability parameter-further comprises a second maximum cost and a second minimum speed to access the third database;
ninth program instructions to assign a third point value to the second cost/speed/probability parameter;
tenth program instructions to determine that the second cost/speed/probability parameter meets or exceeds a third threshold for the third point value;
eleventh program instructions to, in response to the second cost/speed/probability parameter meeting or exceeding the third threshold for the third point value, retrieve the third set of binary data from the third database;
twelfth program instructions to assign a fourth point value to the third binary data based on the amount of information contained in the third binary data;
thirteenth program instructions to sum the second and fourth point values;
fourteenth program instructions to determine that the summation of the second and fourth point values exceeds a fourth threshold;
fifteenth program instructions to, in response to determining that the summation of the second and fourth point values exceeds the fourth threshold, place the current patient into the specific patient readmission cohort; and
sixteenth program instructions to generate a recommendation for an amelioration based on the specific patient readmission cohort to reduce a likelihood of hospital readmission of the current patient within the predefined post-discharge length of time;
and wherein the first, second, third, fourth, fifth, sixth, seventh, eighth, ninth, tenth, eleventh, twelfth, thirteenth, fourteenth, fifteenth, and sixteenth program instructions are stored on the computer readable storage media for execution by the computer processor via the computer readable memory.

12. The system of claim 11, further comprising:
seventeenth program instructions to, in response to determining that the second cost/speed/probability parameter fails to meet or exceed the third threshold for the third point value, transmit an alert that the current patient has not been placed into the specific patient readmission cohort;
and wherein the seventeenth program instructions are stored on the computer readable storage media for execution by the computer processor via the computer readable memory.

13. The system of claim 11, wherein the specific patient readmission cohort is selected from a plurality of patient readmission cohorts, wherein each of the plurality of patient readmission cohorts is defined as having multiple patient attributes, and wherein the system further comprises:
seventeenth program instructions to identify at least one known attribute about the current patient; and
eighteenth program instructions to select the specific patient readmission cohort from a plurality of patient readmission cohorts by matching said at least one known attribute about the current patient to at least one of the multiple patient attributes in the patient readmission cohort;
and wherein the seventeenth and eighteenth program instructions are stored on the computer readable storage media for execution by the processor via the computer readable memory.

* * * * *